United States Patent [19]

Crosbie

[11] Patent Number: 5,069,206
[45] Date of Patent: Dec. 3, 1991

[54] ENDOTRACHEAL TUBE CLUTCH

[76] Inventor: David B. Crosbie, 13228 Highview Dr., Burnsville, Minn. 55337

[21] Appl. No.: 535,515

[22] Filed: Jun. 11, 1990

[51] Int. Cl.$^5$ .............................................. A61M 16/00
[52] U.S. Cl. ........................... 128/207.17; 128/207.14; 128/200.26; 128/DIG. 26; 604/79; 604/174; 604/179
[58] Field of Search .............. 128/207.14, 207.17, 128/200.26, DIG. 26; 251/7; 604/174, 179, 79

[56] References Cited

U.S. PATENT DOCUMENTS

| | | | |
|---|---|---|---|
| 2,127,215 | 8/1938 | Gwathmey | 128/207.14 |
| 2,693,182 | 9/1953 | Phillips | 128/207.14 X |
| 2,857,911 | 11/1956 | Bennett | 128/207.14 X |
| 2,908,269 | 3/1958 | Cheng | 128/207.14 X |
| 3,587,589 | 6/1971 | Ebner | 128/207.14 |
| 3,602,227 | 8/1971 | Andrew | 128/207.17 |
| 3,713,448 | 1/1973 | Arrott | 128/207.17 |
| 3,760,811 | 9/1973 | Andrew | 128/207.17 |
| 3,774,616 | 11/1973 | White et al. | 128/200.26 |
| 3,946,742 | 3/1976 | Eross | 128/207.17 |
| 3,993,081 | 11/1976 | Cussell | 128/207.14 |
| 4,067,331 | 1/1978 | Berman | 128/200.26 |
| 4,170,995 | 10/1979 | Levine et al. | 128/DIG. 26 X |
| 4,191,180 | 3/1980 | Colley et al. | 128/207.17 |
| 4,223,671 | 9/1980 | Muto | 128/200.26 |
| 4,249,529 | 2/1981 | Nestor et al. | 128/207.17 |
| 4,270,529 | 6/1981 | Muto | 128/200.26 |
| 4,326,515 | 4/1982 | Shaffer et al. | 128/207.17 |
| 4,331,143 | 5/1982 | Foster | 128/207.17 |
| 4,351,331 | 9/1982 | Gereg | 128/207.17 |
| 4,356,821 | 11/1982 | Rind | 128/207.14 |
| 4,360,025 | 11/1982 | Edwards | 128/DIG. 26 X |
| 4,397,647 | 8/1983 | Gordon | 604/180 |
| 4,449,527 | 5/1984 | Hinton | 128/207.17 |
| 4,498,903 | 2/1985 | Mathew | 604/174 |
| 4,516,293 | 5/1985 | Beran | 24/16 PB |
| 4,658,814 | 4/1987 | Anderson | 128/207.17 |
| 4,683,882 | 8/1987 | Laird | 128/207.17 |
| 4,698,057 | 10/1987 | Joishy | 604/176 |
| 4,699,616 | 10/1987 | Nowak et al. | 604/180 |
| 4,774,944 | 10/1988 | Mischinski | 128/207.17 |

Primary Examiner—David A. Wiecking
Assistant Examiner—Eric P. Raciti
Attorney, Agent, or Firm—Hugh D. Jaeger

[57] ABSTRACT

Endotracheal tube clutch including a left half, a right half mounted about a living hinge, wings extending out from each half, a semi-circular large hole, small hole and bite block in each half, and a locking assembly for each half for engagement with respect to each other.

4 Claims, 4 Drawing Sheets

ENDOTRACHEAL TUBE CLUTCH

BACKGROUND OF THE INVENTION

1. Field of the Invention

The present invention relates to a medical device, and more particularly, pertains to an endotracheal tube clutch for holding an endotracheal tube in position about a person's mouth.

2. Description of the Prior Art

Prior art endotracheal tubes were previously secured to a person's mouth area so that the tube would not be swallowed by large amounts of adhesive tape or sometimes string. This was very impractical and not pleasant to look at.

Other endotracheal tube devices have been complex devices requiring two hands to operate and have not been easily removable or applyable.

The present invention overcomes the disadvantages of the prior art by providing an endotracheal tube clutch which can be operated with minimal effort and accommodates all sizes of endotracheal tubes, adult tubes and pediatric tubes.

SUMMARY OF THE INVENTION

The general purpose of the present invention is an endotracheal tube clutch which can be easily applied to an adult endotracheal tube, a pediatrics endotracheal tube and can easily be operated, even by one hand.

According to one embodiment of the present invention, there is provided an endotracheal tube clutch including a right half and a left half movable about a living hinge, wing and locking members extending out from the halves, a large hole for an adult endotracheal tube, small hole for a pediatrics tube, and a bite block surrounding the large hole and extending downwardly from the substantially circular member. An optional bite block could also surround the small hole as so desired, and is not illustrated in the drawings for the sake of brevity.

Significant aspects and features of the present invention include an endotracheal tube clutch which can be applied and operated with one hand. The endotracheal tube clutch accommodates all sizes of endotracheal tubes.

Other significant aspects and features of the present invention include a bite block for adult patients. The endotracheal tube clutch also includes a suction access for the pharynx.

Further significant aspects and features of the present invention include an endotracheal tube clutch which can be used with or without a tie down in a hospital setting or a home setting.

Having thus described the embodiments of the present invention, it is a principal object hereof to provide an endotracheal tube clutch.

One object of the present invention is an endotracheal tube clutch which accommodates all sizes of endotracheal tubes, such as, by way of example and for purposes of illustration only, 3 mm to 8.5 mm tubes.

Other objects of the present invention is a endotracheal tube clutch which can easily be removed from the endotracheal tube by one hand.

Still other objects of the present invention is an endotracheal tube which is unaffected by facial hair or body secretions, and maintains the endotracheal tube in a stable position, such as while changing strings in a hospital.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
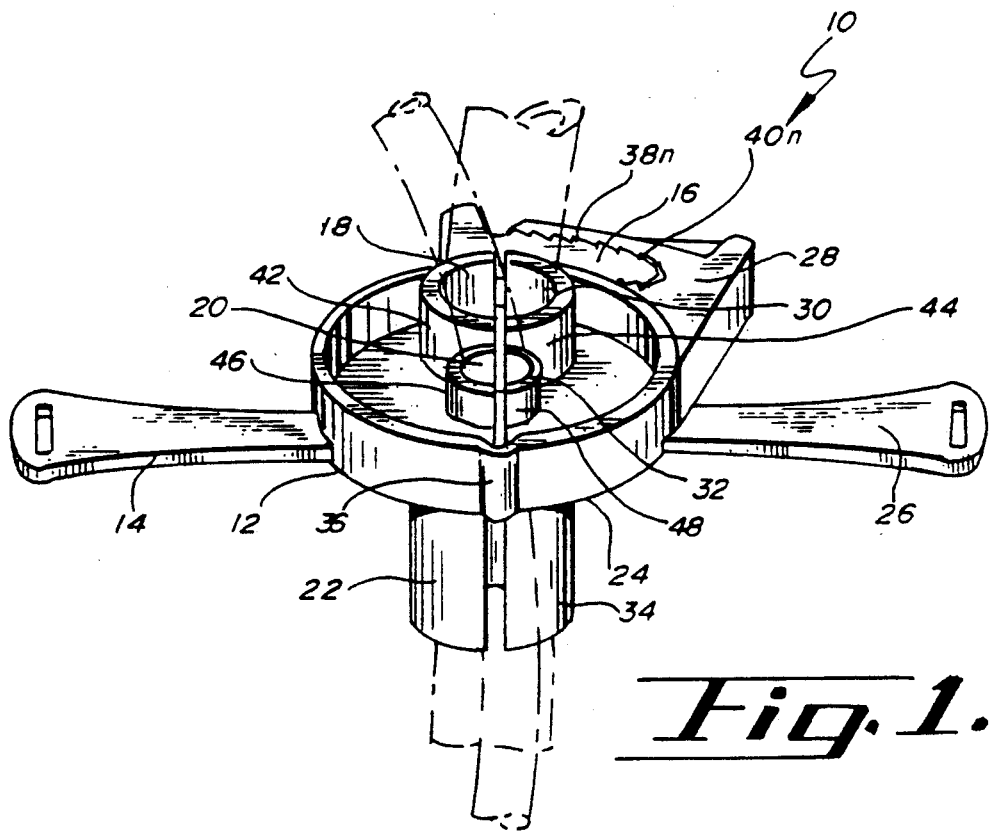
FIG. 1 illustrates a perspective view of an endotracheal tube clutch, the present invention.

FIG. 1 illustrates a perspective view of an endotracheal tube clutch 10 including a left half member 12, a left wing 14 extending outwardly therefrom, a male locking member 16 extending outwardly therefrom, and a semicircular large hole 18 and small hole 20, and a bite block 22. An opposing mirror image right half member 24, including a right wing 26, female locking member 28, a semicircular large hole 30, semicircular small hole 32, and a semicircular bite block 34 are likewise symmetrically positioned with respect to the left half member 12. The left half member 12 and right half member 24 move about a living hinge 36 and lock with respect to each other and with respect to the serrated teeth 38a–38n and the serrated groove 40a–40n. The large holes 18 and 30 and the small holes 20 and 32 can include an upwardly extending cylindrical members 42 and 44 for the large holes 18 and 30 and cylindrical members 46 and 48 for the small holes 20 and 32 to further grasp the endotracheal tube. The clutch can be injection molded from a suitable polymer.

Figure 2:
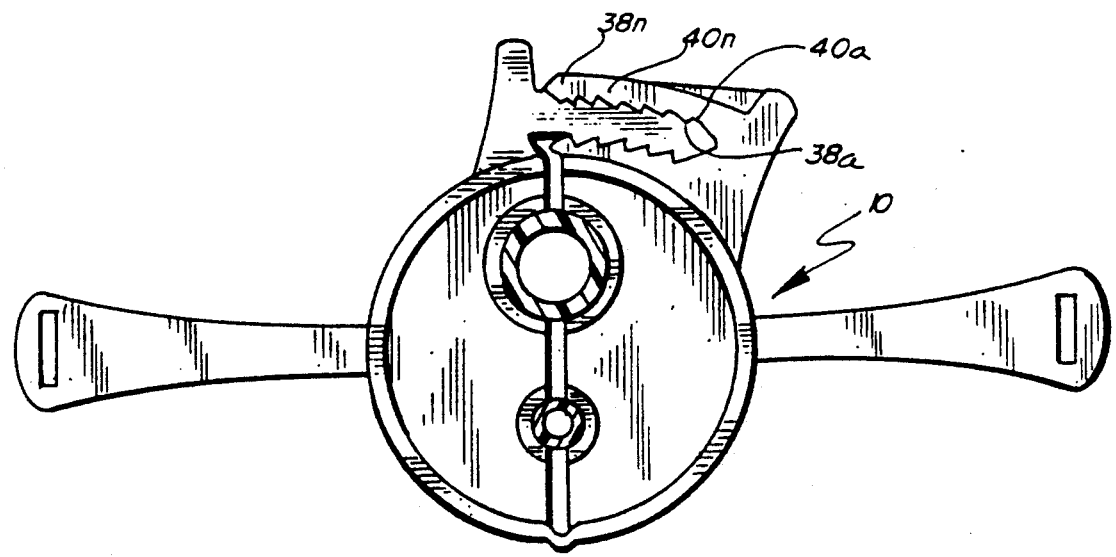
FIG. 2 illustrates a top view.

FIG. 2 illustrates a top view where all numerals correspond to those elements previously described. Particularly illustrated is the adult endotracheal tube clasp or hole for a range of 4.5 mm to 9 mm and a pediatrics tube clasps or hole in a range of 2.5 mm to 4.5 mm. Also illustrated is the relationship of the serrated teeth 38a–38n to the serrated holes 40a–40n.

Figure 3:
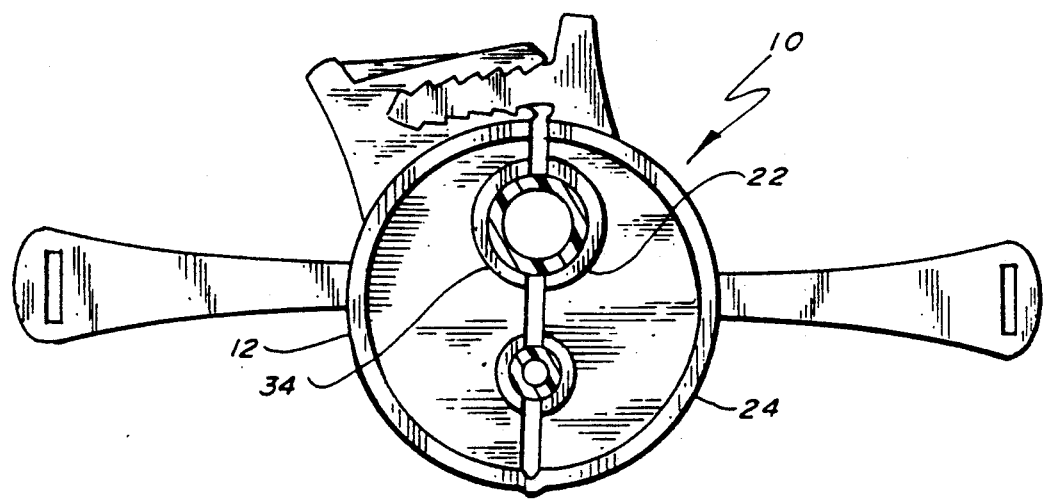
FIG. 3 illustrates a bottom view.

FIG. 3 illustrates a bottom view of the endotracheal tube clutch 10 where all numerals correspond to those elements previously described. Particularly illustrated is the bite block 22 formed by the halves 12 and 24.

Mode of Operation

Figure 4:
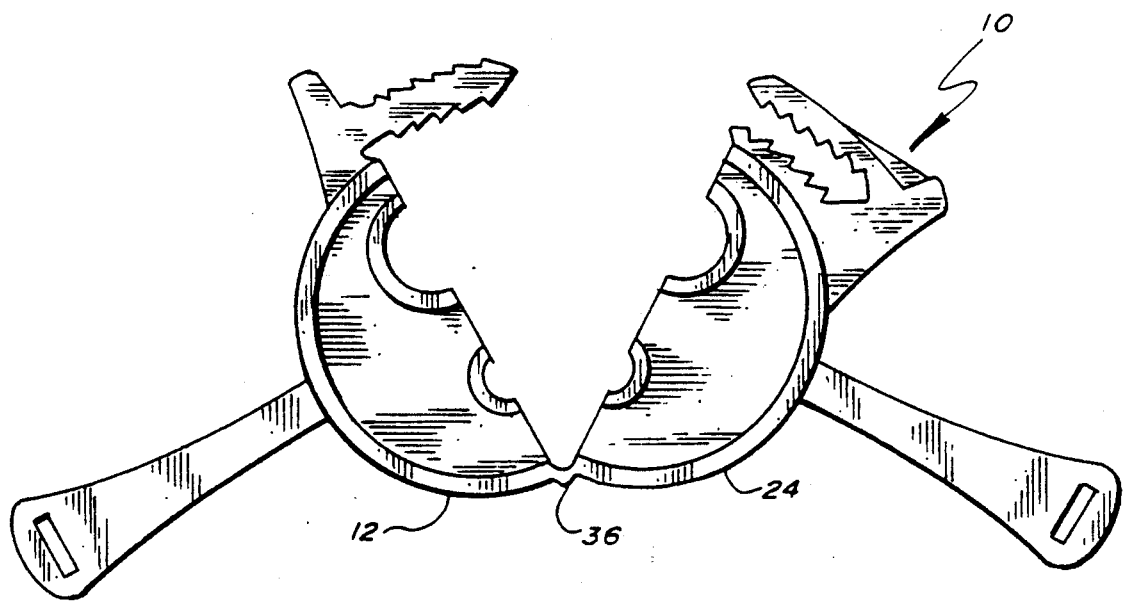
FIG. 4 illustrates a view of the two halves open about a living hinge.

FIG. 4 illustrates a view of the endotracheal tube clutch 10 in an open position where the left half 12 and right half 24 are rotated about the living hinge 36. The endotracheal tube clutch 10 can be molded from a suitable polymer providing for repeated opening and closing and movement about the living hinge 36.

The endotracheal clutch system is best used by applying it loosely to the endotracheal tube prior to intubation and sliding it to the top of the tube. After an intubation has been performed and the tube is established in the proper position within the trachea, the clutch is then slid down the tube to the patient's mouth passing the bite block past the incisors teeth. At this point, the clutch is simply squeezed shut onto the tube by use of the locking members in ratcheting or like action. The clutch can also be easily applied to the tube if the tube is already in place in the patient's trachea.

In the pre-hospital setting, the wings or "depth stop" could be turned perpendicular to the patient's lips and simply taped down. In the hospital setting, it is advised that the wings be turned parallel to the lips and tied down with string.

For pediatric application, the operation would be the same with the exception that the bite block is taken out of use by turning the clutch upside down so the bite block is distal to the patient's mouth.

For removal of the clutch, move on side of the ratchet locking members up, and the other side of the ratchet locking teeth down or vice versa. It does not make any difference which side goes up or down, just so that the wings move in opposite directions to separate for subsequent rotation about the living hinge and away from the tracheal tube.

Figure 5:
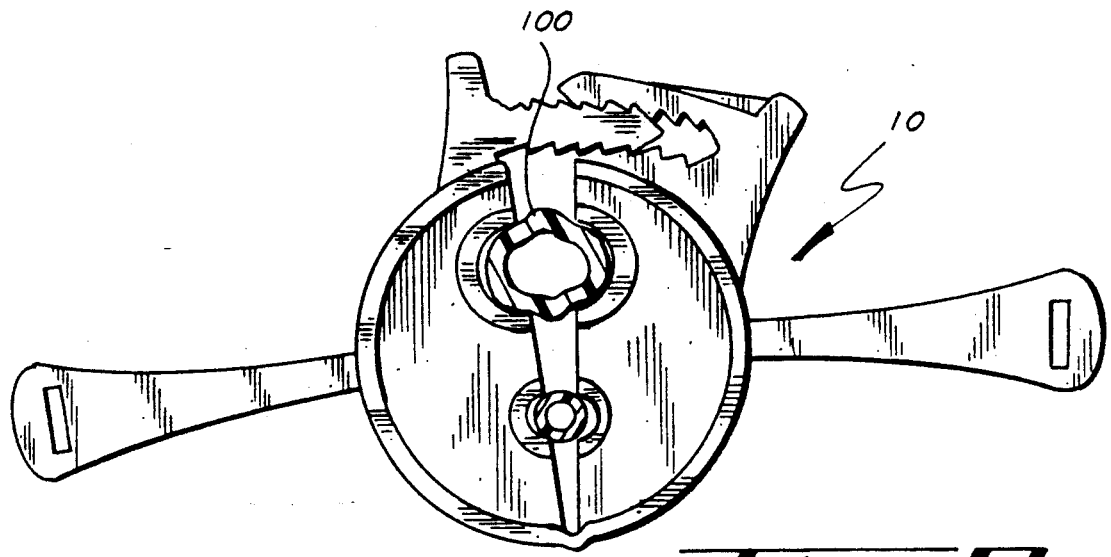
FIG. 5 illustrates the two halves closed.

FIG. 5 illustrates the endotracheal tube clutch 10 closed about an endotracheal tube 100.

Figure 6:
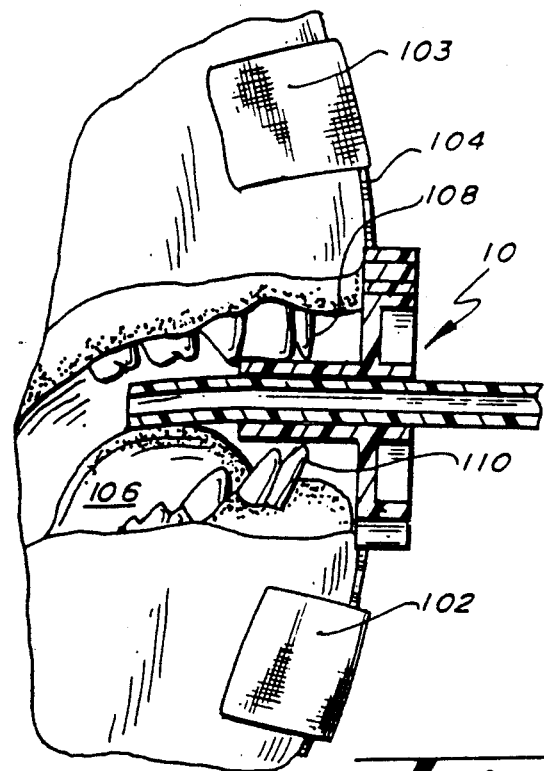
FIG. 6 illustrates a cross-sectional view.

FIG. 6 illustrates a side view of the endotracheal tube clutch 10 secured by tape 102 and 103 to a person's face 104 and grasping a endotracheal tube 100. The tongue 106 is also illustrated, as well as upper teeth 108 and lower teeth 110.

Figure 7:
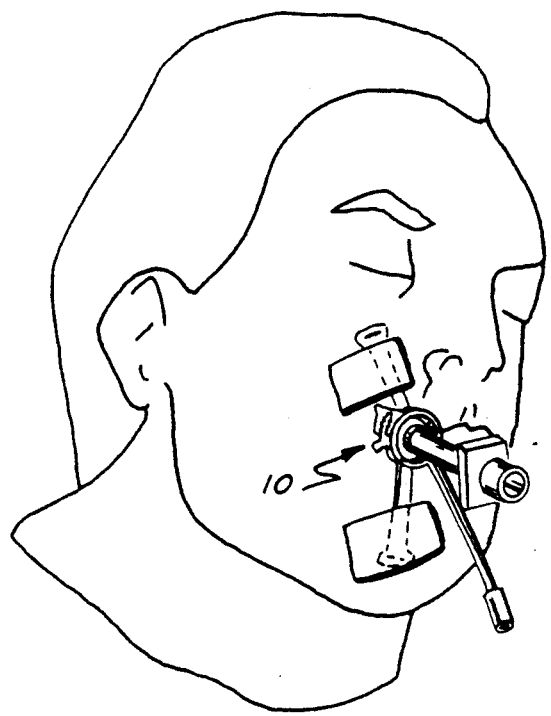
FIG. 7 illustrates a pre-hospital use view.

FIG. 7 illustrates a perspective view of the endotracheal tube clutch 10 taped to a person's face grasping an endotracheal tube 100.

Figure 8:
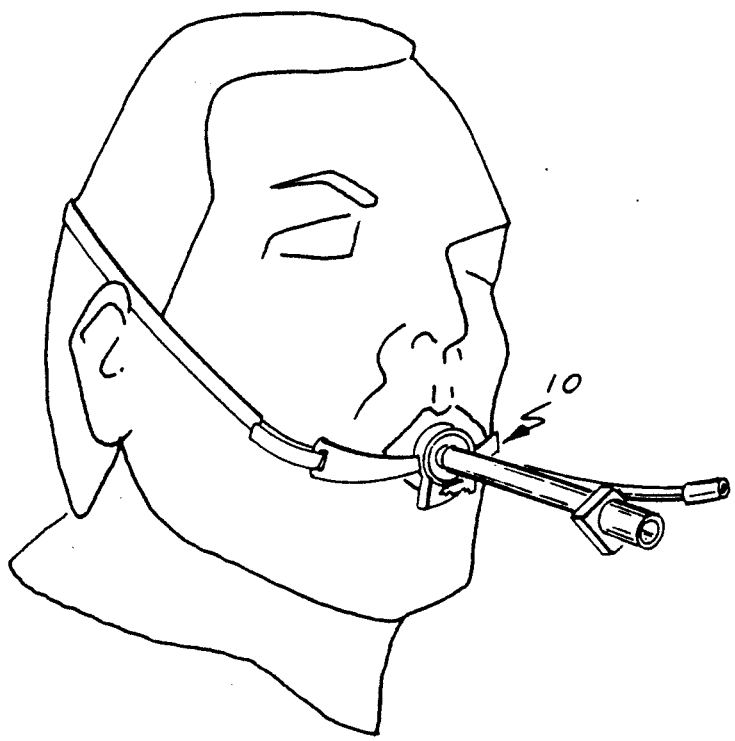
FIG. 8 illustrates a hospital use view.

FIG. 8 illustrates a perspective view of the endotracheal tube clutch 10 grasping an endotracheal tube 100 and tied down about a person's head.

Various modifications can be made to the present invention without departing from the apparent scope hereof.

I claim:

1. Endotracheal tube clutch for gripping an adult endotracheal tube or a pediatric endotracheal tube comprising:

a. a semicircular left half member including a left wing, a male locking member with a plurality of serrated teeth, a large semicircular hole and a partial cylindrical member extending upwardly about said large hole, a small circular hole and a partial cylindrical member extending upwardly about said small hole, and a semicircular bite block extending downwardly about said large hole;
   b. a semicircular right half member including a right wing, a female locking member with a plurality of serrated grooves, a large semicircular hole and a partial cylindrical member extending upwardly about said large hole, a semicircular small hole and a partial cylindrical member extending upwardly about said small hole and a semicircular bite block about said large hole; and,
   c. a living hinge connecting one end of said left half member to one end of said right half member whereby movement about said living hinge causes said left half member and said right half member to engage with respect to each other forming holes with surrounding cylindrical members for engaging endotracheal tubes, as well as forming a bite block about said large hole.

2. Process for maintaining an endotracheal tube in a person's mouth comprising the steps of:

a. inserting an endotracheal tube into a person's mouth and about the pharynx;
   b. positioning an endotracheal tube clutch about the endotracheal tube;
   c. moving corresponding semicircular halves of said endotracheal tube clutch about a living hinge;
   d. engaging said male locking member into said female locking member; and,
   e. tying a string from wings extending outwardly from each semicircular halve about a person's head.

3. Process of claim 2 comprising the step of inserting the bite block of said endotracheal tube clutch into a person's mouth.

4. Process of claim 2 including the step of taping down wings of said endotracheal tube clutch to a person's face.

* * * * *